United States Patent [19]
Benjamin

[11] 4,094,571
[45] June 13, 1978

[54] GROUNDING CABLE CLIP

[75] Inventor: Thomas A. Benjamin, Glen Gardner, N.J.

[73] Assignee: IPCO Hospital Supply Corporation, White Plains, N.Y.

[21] Appl. No.: 787,835

[22] Filed: Apr. 15, 1977

[51] Int. Cl.² .............................................. H01R 13/54
[52] U.S. Cl. ................................... 339/91 R; 128/416; 339/113 R
[58] Field of Search ................................ 120/416–418, 120/419, 420; 339/75 R, 91 R, 113 R, 113 L

[56] References Cited

U.S. PATENT DOCUMENTS

| 3,085,577 | 4/1963 | Berman et al. | 128/416 X |
| 3,624,590 | 11/1971 | Bolduc | 339/75 R |
| 3,642,008 | 2/1972 | Bolduc | 128/416 |
| 3,699,968 | 10/1972 | Bolduc | 339/75 R X |
| 3,842,394 | 10/1974 | Bolduc | 339/75 R |

Primary Examiner—Roy Lake
Assistant Examiner—E. F. Desmond
Attorney, Agent, or Firm—Holland, Armstrong, Wilkie & Previto

[57] ABSTRACT

A grounding cable clip which may be easily snapped onto and removed from a grounding pad and which may be used to monitor the circuit continuity before and during its application to the patient.

26 Claims, 12 Drawing Figures

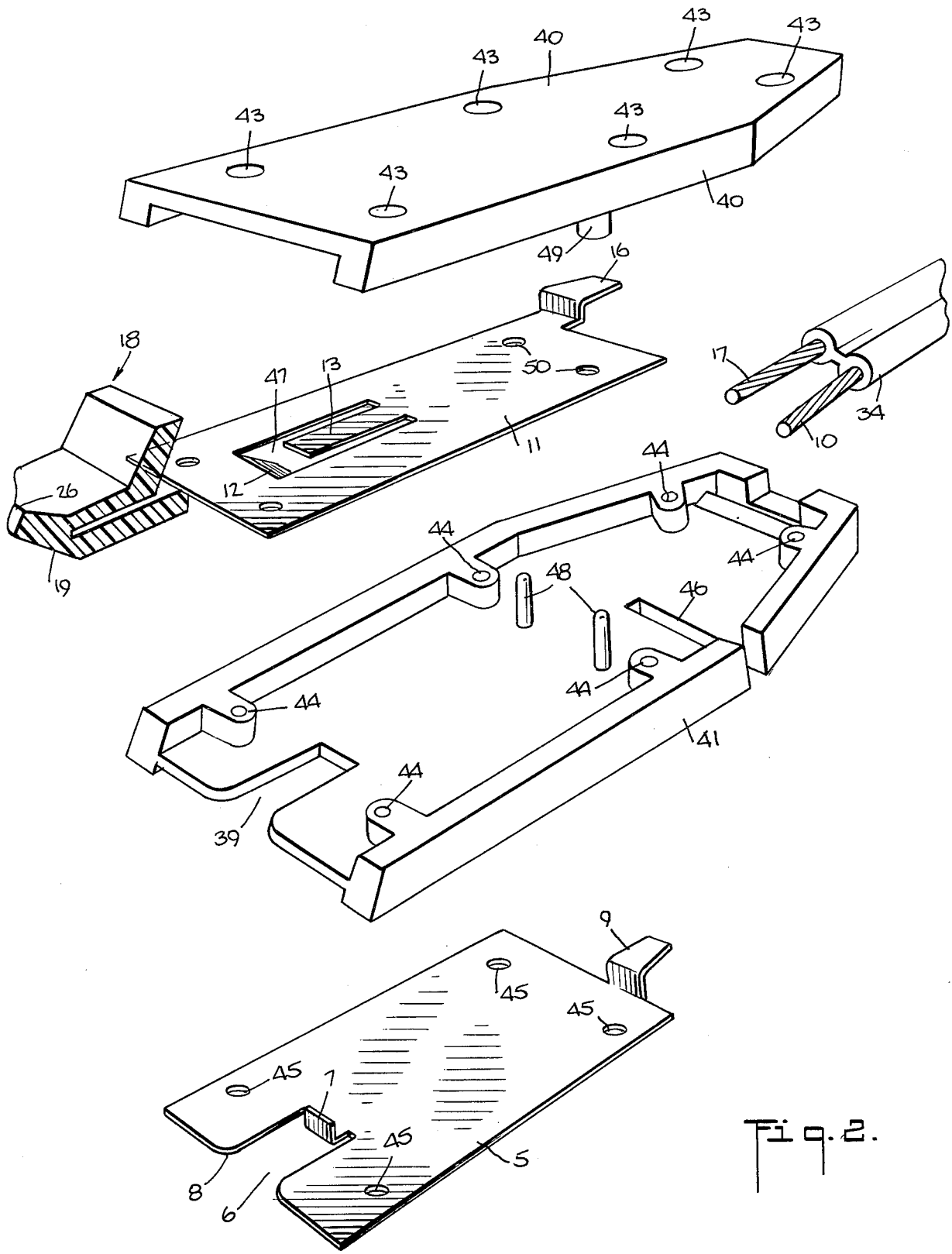

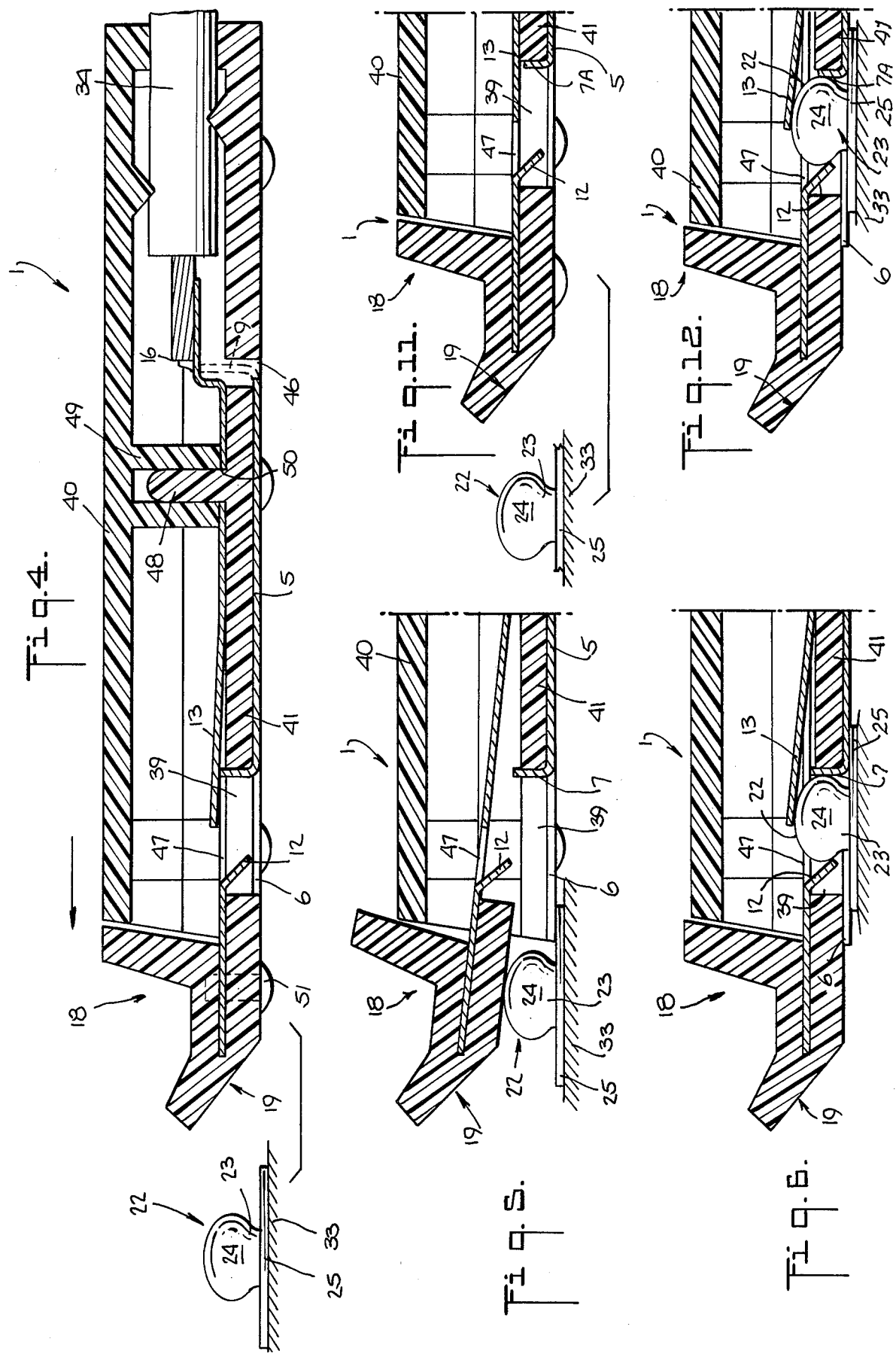

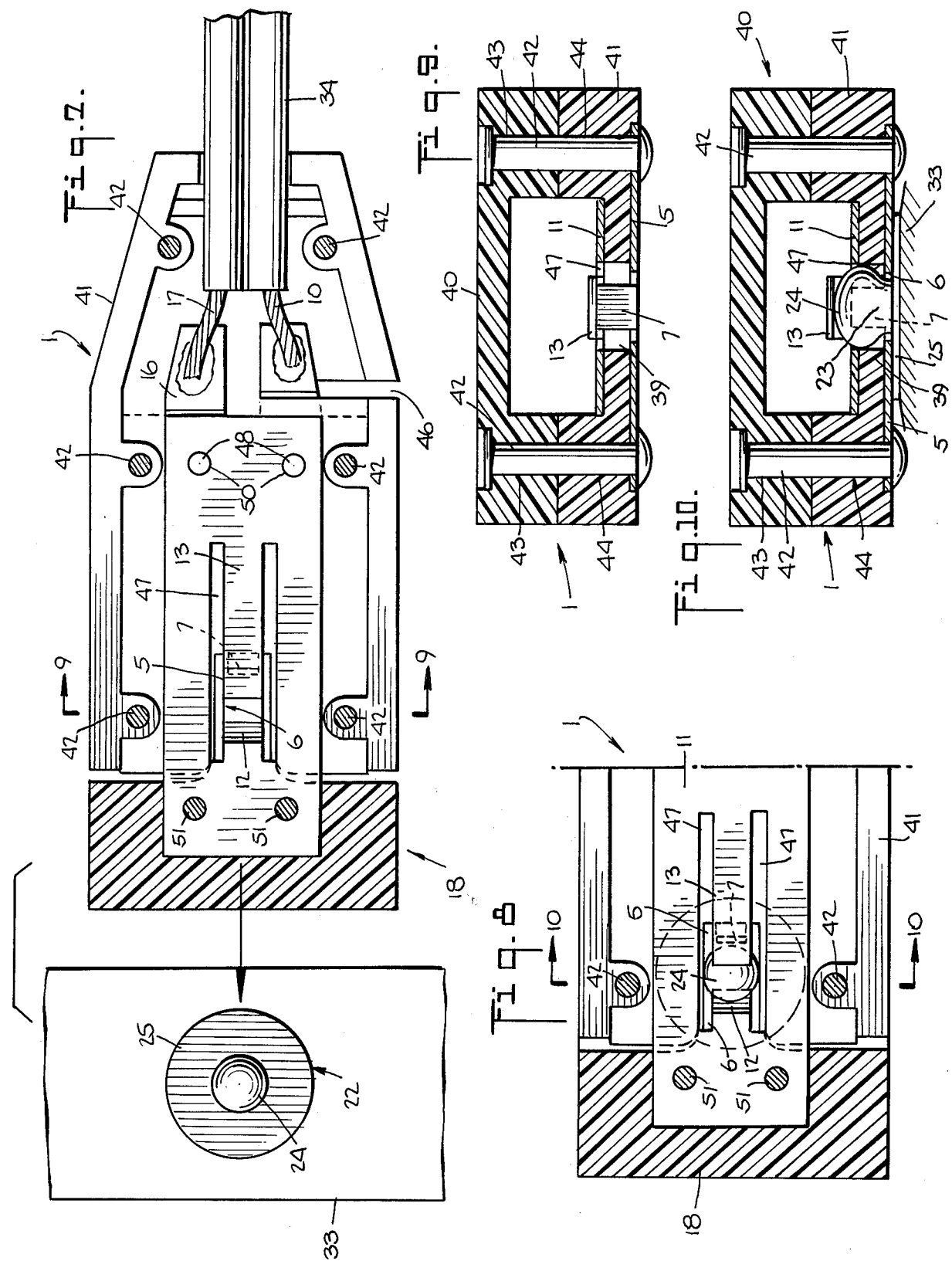

GROUNDING CABLE CLIP

DESCRIPTION

The present invention relates to an improved grounding cable clip for use in electrosurgical procedures.

Electrosurgical procedures which are gaining popularity in hospitals require a grounding pad to complete the circuit from the electrosurgical generator through the patient and back to the electrosurgical generator. Efficient functioning and safety of electrosurgical machines depends upon an unimpaired return of current via the ground pad and its cable. If this fails, the current will choose the next best route, which will mean a short circuit to ground with consequent risk of a diatherm burn.

Some machines are equipped with a ground test stud that requires the operating staff to check the circuit before each operation. This system only monitors the continuity of the cable and its attachment to the ground electrode. It does not monitor the electrical contact and conducivity between the ground electrode and the patient.

A large percentage of these grounding pads are preferably disposable. The most common method of attaching the disposable grounding pad to the electrosurgical generator is by means of a grounding cable which is clipped to a metal snap button located on the disposable grounding pad.

Grounding cables currently being used present several problems. Insecure attachment of the cable to the pad results in poor electrical contact and the possibility of accidental disconnection from the pad. Complicated toggle or spring loaded clamps require close tolerances or exceptionally strong hands to apply the cable to the grounding pad.

Large, bulky clips may protrude from the pad and may cause snagging in surgical drapes or may place undue strain on the grounding pad. Some cables offer no means of checking electrical continuity while those cables providing a continuity monitoring system must be fastened to a grounding pad to check electrical continuity.

The object of this invention is to provide an in grounding cable clip which will eliminate the drawbacks outlined above.

Another object of the present invention is the provision of an improved grounding cable clip which permits easy, one-hand attachment to and removal from the grounding pad.

Another object of the present invention is the provision of an improved grounding cable clip which permits positive, secure attachment and electrical contact when properly applied.

Another object of the present invention is the provision of an improved grounding cable clip which permits small, physical size to reduce the possibility of excessive strain on the grounding pad.

Another object of the present invention is the provision of an improved grounding cable clip which permits monitoring of electrical continuity when detached from a grounding pad.

Another object of the present invention is the provision of an improved grounding cable clip which permits monitoring of electrical continuity through the grounding pad contact when attached to the grounding pad.

Other and further objects of the invention will be obvious upon an understanding of the illustrative embodiment about to be described, or will be indicated in the appended claims, and various advantages not referred to herein will occur to one skilled in the art upon employment of the invention in practice.

A preferred embodiment of the invention has been chosen for purposes of illustration and description and is shown in the accompanying drawings forming a part of the specification, wherein:

FIG. 2 is an exploded perspective view of the clip shown in FIG. 1.

FIG. 4 is a sectional view taken along line 4—4 of FIG. 1.

FIG. 5 is a sectional view similar to FIG. 4 showing the clip about to engage the grounding pad snap button.

FIG. 6 is a sectional view similar to FIG. 4 showing the clip in full engagement with the grounding pad snap button.

FIG. 7 is a top view showing the clip in the same position as in FIG. 4.

FIG. 8 is a fragmentary top view showing the clip fully engaged on the grounding pad snap button.

FIG. 9 is a sectional view taken along line 9—9 of FIG. 7.

FIG. 10 is a sectional view taken along line 10—10 of FIG. 8.

FIG. 11 is a fragmentary side sectional view similar to FIG. 4 showing a modification of the present invention.

FIG. 12 is a view similar to FIG. 6 showing the clip fully engaged on the grounding pad snap button.

Figure 1:
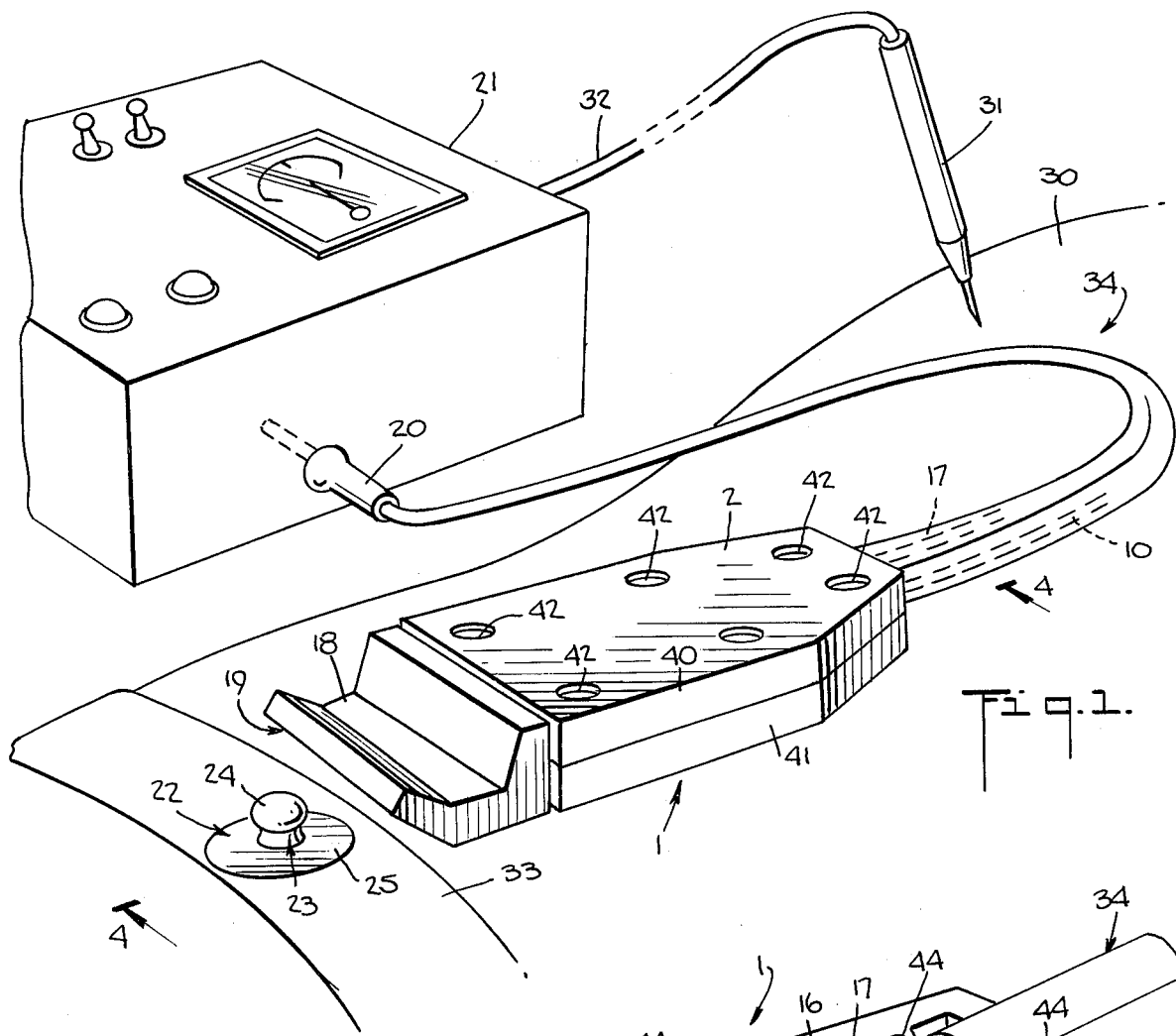
FIG. 1 is a perspective view showing the cable clip of the present invention about to be placed in use on a patient.
Figure 3:
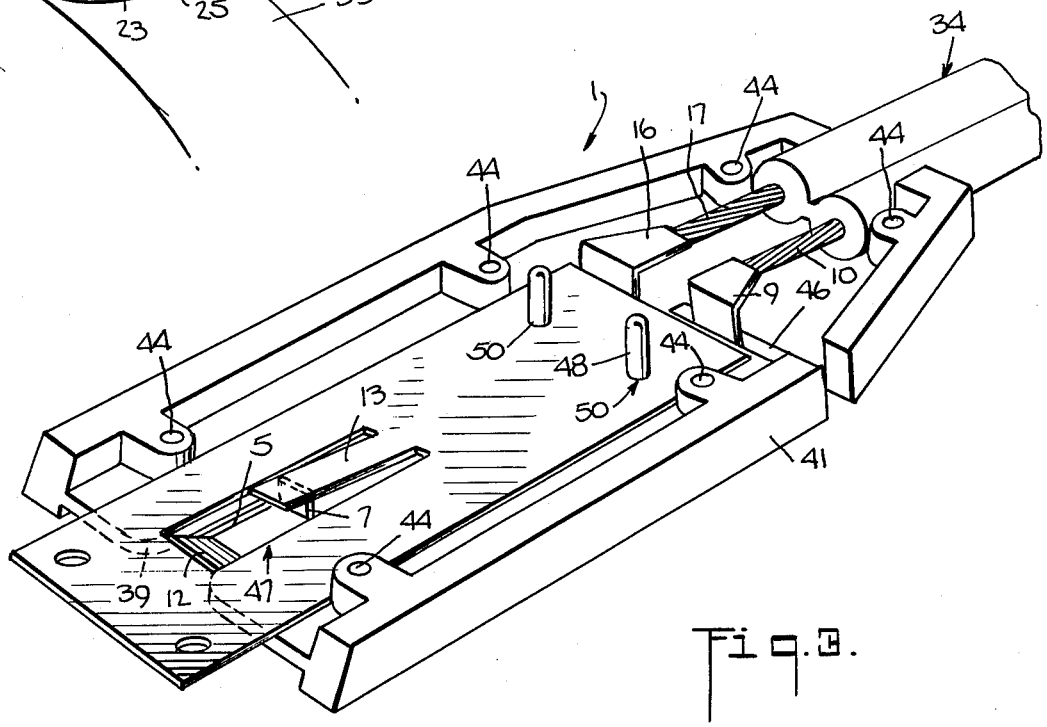
FIG. 3 is a perspective view of the clip with the top cover removed.

Referring to the drawings, there is shown in FIG. 1 the present invention in position when used in operating on a patient 30. High-frequency current is obtained from a control assembly 21 which is connected to power supply (not shown). The operating electrode 31 is connected to the control assembly 21 by a cable 32.

The circuit through the patient 30 is completed with a grounding pad 33 located in contact with an area of the skin of the patient 30. A cable 34 comprising monitoring wire 10 and grounding wire 17 is connected to the grounding pad 33 through a clip 1 and snap button 22. The clip 1 is clamped to a snap button 22 on the grounding pad 33 to complete the electric circuit to the control assembly 21. The opposite end of cable 34 is connected to a test and control circuit (not shown) which may be located in the control assembly 21. Prior to using the operating electrode 31, the control circuit will be tested to see if the releasable clip 1 is in electrical contact with the grounding pad 33 and determine if high voltage is present in the operating circuit.

The clip 1 comprises housing 2 of an electrically non-conductive material, such as a plastic, having a top 40 and a bottom 41 which are adapted to be held together by fastening means such as rivets 42 in openings 43 and 44.

A metal monitor retaining shoe 5 is provided having a centrally located slot 6 extending from one end thereof with curved mouth 8 and an upstanding retaining shoe tab 7. The shoe 5 is mounted below the clip 1 by means of the rivets 42 extending through openings 45. A connecting tab 9 is provided which extends rearwardly and upwardly through slot 46 in the bottom 41 for connection to monitoring wire 10. The slot 6 is made to be in alignment with slot 39 in bottom 41 when the two are connected together.

A spring metal power clip 11 is provided which has opening 47. At its front edge the opening 47 has a downwardly angled latch tab 12. A resilient contact 13 extends from the rear edge of opening 47 and is of sufficient length to provide contact with snap button 23 when in place. A connecting tab 16 extending from the rear of plate 11 is adapted to be electrically connected to a grounding wire 17 in cable 34. The plate 11 is mounted on the bottom portion 41 of the clip and held in place by pin and sockets 48 passing through openings 50 in the plate and extending into sockets 49. A power clip knob 18 is attached to the front end of the plate 11 by means of rivet 51 and is provided with an upwardly directed ramp 19 to aid in attachment and removal to the snap button 22.

The grounding pad 33 has the snap button or connector 22 attached thereto by a flange 25. The snap button 22 has an enlarged head 24 and a reduced diameter neck portion 23 interposed between the flange 25 and the head 24.

In the embodiment shown in FIGS. 1 to 10, the shoe tab 7 extends upwardly for a distance greater than the thickness of the housing bottom 41 so that it normally strikes and maintains contact with the tongue 13 as shown in FIGS. 4, 7 and 9. In this manner, electrical continuity of the power clip plate 11, grounding cable 17, grounding cable plug 20, and control assembly 21 can be monitored without connecting the clip 1 to grounding pad 33. The monitoring current passes from control assembly 21 through monitoring wire 10 to retaining shoe 5, then through retaining shoe tab 7, which is in normal contact with power clip 11 through its tongue 13. The monitoring signal passes through the power clip 11, the grounding wire 17, the plug 20 and back into the monitoring circuitry of the generator 21. Any break in this circuitry will be signalled by the monitor (not shown) isolating the fault to the cable circuit and eliminating suspicion of the cable-to-grounding-pad connection.

To attach the cable 34 to the snap button 22 of the grounding pad 33, the grounding clip 1 is pushed laterally toward the grounding pad snap button 22 as shown in FIGS. 4 and 7. Keeping the snap button 22 approximately centered on the power clip knob 18, the power clip knob 18 is moved over the head 24 of the snap connector 22, as shown in FIG. 5. The ramp 19 strikes the head of the snap button 22 raising the knob 18 and the power clip plate 11 to which it is attached. This raises the tongue 13 off retaining shoe tab 7 to break electrical contact therewith. As the clip 1 is moved further toward the snap button 22, the button 22 enters the slot 6 through mouth 8 in the retaining shoe 5 and the slot 39 in lower housing 41. The head 24 makes contact with the tongue 13 as well as the tab 7. The slot 6 in the retaining shoe 5 is wide enough to contact both sides of the reduced neck portion 23 of the snap button 22 to make electrical contact between plates 5 and 11 and to prevent vertical removal of the grounding clip assembly 1 over the head portion 24 of the snap connector 22. As shown in FIG. 6, when the grounding clip assembly 1 is moved completely onto the snap connector 22, the power clip latch tab 12 drop downward behind the neck portion 23 to hold the snap button in place.

The snap connector 22 prevents contact tongue 13 from touching retaining shoe tab 7 and the monitoring circuit will now monitor continuity through the snap button 22 indicating good contact between the grounding clip assembly 1 and the grounding pad snap connector 22. This monitor circuit passes through the monitor wire 10 the retaining shoe 5, the snap connector 22, the power clip contact tongue 13, and back to the control assembly 21 via the grounding wire 17 bypassing the discontinuity between the contact tongue 13 and the retaining shoe tab 7.

The snap connector 22 is trapped in the grounding clip assembly 1 by the slot 6 which prevents lateral and vertical movement, by the latch tab 12 which prevents rearward movement out the slot, and by the retaining shoe tab 7 at the end of the slot 6 to prevent further forward movement. Monitoring circuitry and grounding circuitry are complete and the unit is ready for use.

In the embodiment shown in FIGS. 11 and 12, the embodiment of the invention is not adapted to monitor the circuit when the clip is not attached to the pad 33. In FIG. 11, the tab 7A in this embodiment is shorter than the tab 7 in FIGS. 1 to 10 so that when the tongue 13 is at rest tab 7A will not be in contact with the tongue 13. Hence the circuit is not made when the clip is not attached to the snap button 27. However, when the clip is attached to the snap button 22, the tongue 13 and the tab 7A will still contact the head 25 so that the monitoring can occur when the clip is on the snap button 22.

It will be seen that attachment of the grounding cable clip 1 can be accomplished very quickly using one hand. Firm and secure attachment is signalled audibly, by a "click" as the power clip drops over the snap connector 22, visually, by the return of the power clip knob 18 to its at rest position, and electrically, by the monitor circuit. When attached, the grounding cable clip is free to rotate about the vertical axis of the snap connector 22 reducing a source of strain on the grounding pad.

After use, the grounding cable clip is removed from the snap connector by lifting upward on the power clip knob lip 26 with the index finger and pulling the clip 1 backward with the finger and the thumb. This removal may be accomplished very quickly by using one hand.

It will be seen that the present invention provides a grounding cable clip which can be applied by one hand with a simple sliding motion and can be removed with one hand by lifting the knob and sliding the unit backward. The clip of the present invention will monitor cable electrical continuity without being attached to a grounding pad and will monitor electrical continuity between the grounding wire and the grounding pad when attached.

The present invention also provides a grounding cable slip which will signal mechanical and electrical connection to the snap button audibly with a click as well as visually by position of the power clip knob and which has a low profile to prevent snagging and accidental strain on the grounding pad and is of small size and simple construction for economy.

The present invention also provides a grounding cable clip which will rotate freely and also prevent accidental strain on the grounding pad and, when properly applied, is securely locked to the grounding pad and a clip which has a ramp to automatically open the clip to accept the snap button as the clip is slid toward the connector and to accomodate a finger to raise the power clip knob for removal.

As many and varied modifications of the subject matter of this invention will become apparaent to those skilled in the art from the detailed description given hereinabove, it will be understood that the present invention is limited only as provided in the claims appended hereto.

What is claimed is:

1. A grounding cable clip comprising a power plate and a monitor retaining shoe, said plate and shoe being spaced from each other, said shoe having an upstanding tab portion, said plate having a resilient tongue overlying the tab portion, said shoe having means for receiving a grounding pad connector, said resilient tongue being in position to contact a grounding pad connector when received in the shoe.

2. A clip as claimed in claim 1 wherein said shoe has a front end and a rear end and wherein a slot is located in the front end.

3. A clip as claimed in claim 2 wherein the tab extends upwardly from the rear end of the slot.

4. A clip as claimed in claim 3 wherein said shoe and said plate are superimposed relative to each other and are separated from each other by insulating material.

5. A clip as claimed in claim 4 wherein said plate has an opening therein adapted to overlie the slot in the shoe.

6. A clip as claimed in claim 5 wherein the said plate has a resilient tongue extending into said opening and adapted to overlie the tab of the shoe.

7. A clip as claimed in claim 6 wherein said tab extends upwardly so that it is in contact with the tongue.

8. A clip as claimed in claim 7 wherein said plate has a front clip knob mounted thereon.

9. A clip as claimed in claim 8 wherein said clip knob has a front ramp extending upwardly therefrom.

10. A clip as claimed in claim 9 wherein a housing is provided for the clip, said housing comprising an upper portion and a lower portion and wherein the plate is mounted between the said two portions and the shoe is mounted beneath the bottom portion.

11. A clip as claimed in claim 10 wherein said bottom portion has a slot in substantial superimposed alignment with the slot in the shoe and the opening in the plate.

12. A clip as claimed in claim 11 wherein said tab extends upwardly through said slot.

13. A clip as claimed in claim 12 wherein the opening in the plate has a front lock tab extending inwardly and downwardly therefrom.

14. A clip as claimed in claim 13 wherein said snap connector is adapted to be received in the slots in the shoe and the lower portion of the housing whereby, when fully inserted, the snap connector will strike the tongue and lift it upwardly out of contact with said tab.

15. A clip as claimed in claim 14 wherein said connector has a narrow neck portion and an enlarged head portion and wherein the neck portion is in said slot and the depressed tab is behind said slot.

16. A clip as claimed in claim 15 wherein connections of the shoe and the plate to the monitor wire and the ground wire is made within said housing and a cable containing these two wires extends from the housing into a generator.

17. A clip as claimed in claim 6 wherein said tab extends upwardly for a distance less than the separation between said plate and said shoe so that it is out of contact with the tongue.

18. A clip as claimed in claim 17 wherein said plate has a front clip knob mounted thereon.

19. A clip as claimed in claim 18 wherein said clip knob has a front ramp extending upwardly therefrom.

20. A clip as claimed in claim 19 wherein a housing is provided for the clip, said housing comprising an upper portion and a lower portion and wherein the plate is mounted between the said two portions and the shoe is mounted beneath the bottom portion.

21. A clip as claimed in claim 20 wherein said bottom portion has a slot in substantial superimposed alignment with the slot in the shoe and the opening in the plate.

22. A clip as claimed in claim 21 wherein said tab extends upwardly through said slot.

23. A clip as claimed in claim 22 wherein the opening in the plate has a front lock tab extending inwardly and downwardly therefrom.

24. A clip as claimed in claim 23 wherein said snap connector is adapted to be received in the slots in the shoe and the lower portion whereby when fully inserted the snap connector will strike the tongue and lift it upwardly.

25. A clip as claimed in claim 24 wherein said connector has a narrow neck portion and an enlarged head portion and wherein the neck portion is in said slot and the depressed tab is behind said slot.

26. A clip as claimed in claim 25 wherein connections of the shoe and the plate to the monitor wire and the ground wire is made within said housing and a cable containing these two wires extends from the housing into a generator.

* * * * *